United States Patent [19]

Hlusko

[11] Patent Number: 4,745,926
[45] Date of Patent: May 24, 1988

[54] REFLUX PANTS

[76] Inventor: Dana L. Hlusko, 5312 Marlington Dr., Virginia Beach, Va. 23462

[21] Appl. No.: 853,887

[22] Filed: Apr. 21, 1986

[51] Int. Cl.⁴ .............................................. A61F 5/37
[52] U.S. Cl. ........................................ 128/134; 2/328
[58] Field of Search .......................... 2/326, 327, 328; 128/133, 134, 135, 33, 68, 75; 5/424, 494

[56] References Cited

U.S. PATENT DOCUMENTS

| | | | |
|---|---|---|---|
| 1,574,672 | 2/1926 | McCarroll-Doull | 128/134 |
| 1,904,480 | 4/1933 | Leffert | 128/134 |
| 1,930,378 | 10/1933 | Beagan | 128/134 |
| 2,853,068 | 8/1958 | Povel | 128/134 |
| 3,034,502 | 5/1962 | Lund | 128/134 |
| 3,641,997 | 2/1972 | Posey, Jr. | 128/134 |
| 4,050,737 | 8/1977 | Jordan | 128/134 X |
| 4,051,854 | 10/1977 | Aaron | 128/DIG. 15 X |
| 4,117,840 | 10/1978 | Rasure | 128/134 |
| 4,471,761 | 8/1984 | Guimond | 128/134 |
| 4,657,005 | 4/1987 | Williamson | 128/134 |

OTHER PUBLICATIONS

MRI Corporation, "GER Harness" (Brochure) Powell, TN 37849, 1984.

Primary Examiner—Richard J. Johnson
Attorney, Agent, or Firm—Sandler & Greenblum

[57] ABSTRACT

Reflux pants for maintaining an infant having gastroesophageal reflux at a predetermined position on an inclined surface which includes straps for stabilizing the upper torso of the infant. The straps are adapted to be removably attached to the inclined bed for maintaining the infant in the predetermined given upright position on the inclined bed. Tabs are included on the straps and safety pins are pinned to the tabs for removably attaching the straps to the inclined bed. A diaper-shaped portion is connected to the straps for supporting the lower torso in the predetermined position.

7 Claims, 3 Drawing Sheets

REFLUX PANTS

TECHNICAL FIELD

The present invention relates to a pair of reflux pants for treatment of an infant with gastroesophageal reflux.

BACKGROUND ART

Reflux occurs frequently in premature babies due to the weakness of the esophageal sphincter. When the infant is fed, formula can easily be regurgitated into the esophagus, into the trachea and aspirated by the infant causing aspiration pneumonia. The treatment for infants with gastroesophageal reflux, among other things, is to position the infant face down on a bed. The head of the bed is maintained in a raised position so that gravity may assist in keeping the stomach contents in the stomach.

However, the infant can not remain in the bed in the correct upward position on his own, and repeatedly slides either sideways or down towards the foot of the bed. When the infant slides down or to the side, he or she is no longer in the proper position for this type of treatment to be effective. The reflux pants of the present invention are used to keep the baby stationary so that the treatment will be efficient.

Until the present time, blankets, T-shirts and sandbags have been used to keep the infant in the desired position. The infant can be wrapped in blankets or surrounded by sandbags. The T-shirts are used upside-down with the legs of the infant placed through the armholes of the T-shirts. However, these methods are ineffective for a variety of reasons. The infant slides out of the blankets, the sandbags are uncomfortable and both the sandbags and T-shirts cause the babies legs to be abnormally positioned. The abnormal leg position may cause future development of orthopedic problems.

U.S. Pat. No. 4,471,767 to GUIMOND discloses a therapeutic device for positioning an infant afflicted with gastroesophageal reflux. The device includes an incline flat bed portion covered with foam pad 15, as illustrated in FIG. 1 of the patent. Sides 3 and 5 are covered by plastic covered foam pads 11 and 13, respectively. A pair of generally angled mount support rods are provided to attach a pair of plastic pants 23, via eye screw 17, to the inclined flat surface.

U.S. Pat. No. 2,853,068 to POVEL discloses a safety blanket for children which includes main blanket portion B which is adapted to be suspended over the shoulders of a child. Bands C are provided for tying the blanket to a bed, and cross strap D is attached to the blanket. Straps B are positioned over the shoulders of a child in a generally suspender-type fashion. Additional bands C' can be provided to attach belt E to the blanket.

U.S. Pat. No. 3,034,502 discloses an infant holder which adapted to limit the movement of humans and animals during treatment or other operations. The invention includes a main body portion 10 having an upper end and cuts 13 and 14 forming wings 17 and 18 between the cuts and the bottom of the body. The wings are adapted to be bent upwardly to permit legs of a child to be inserted therein. The restraining portion of the device includes a pair of upper straps 25 and 26 which can be flexibly positioned around the shoulder, chest and thorax of a child to retain the child with limited mobility. A flap 33 is provided for receiving the head of a child.C U.S. Pat. No. 4,050,737 discloses a support harness for a child which includes a main portion 21, shoulder straps 32, and the base support portion 31. VELCRO straps 33 and 34 are provided for attaching shoulder straps 32 to straps 27 located about the chair in which the child is positioned.

None of the previous methods and devices used for restraining infants provide a device by which an infant can be restrained on an inclined bed where both the main torso and the chest are supported.

DISCLOSURE OF INVENTION

It is an object of the present invention to provide reflux pants which are less complicated than the prior art devices and which can be used on any type of bed.

It is another object of the present invention to provide reflux pants which are suited for isolettes and radiant warming beds used with premature babies.

The object of the present invention to provide reflux pants which are provided in one size which can fit a variety of babies.

It is another object of the present invention to provide reflux pants which provide VELCRO fasteners at the side so that diapers may be changed without completely repositioning the baby. This feature is particularly important when the baby is on a ventilator or has a tube in its mouth and which leads into its lungs. These tubes can be pulled out rather easily and the child can be changed with less manipulation.

It is further an object of the present invention to provide reflux pants having a cross-over strap and a short strap that is safety-pinned to the inclined bed to help stabilize the chest of the infant. Without these straps, the infant can slip to one side or the other in the bed, which defeats the purpose of the treatment.

It is further an object of the present invention to provide reflux pants which allow a large portion of the body surface of the infant to be exposed for observation, which is essential in sick babies.

The reflux pants, for premature babies weighing less than 2500 grams, are patterned after a diaper with straps attached. The bottom portion is diaper shaped. The top portion consists of H-shaped straps fastened to the front. The straps cross over in the back and attach to the back of the diaper portion using VELCRO. The sides of the diaper include VELCRO strips to make changing the baby simple. On the front of the H-shaped straps are tabs that can be pinned to the bed to prevent the baby from sliding in any direction.

According to an embodiment of the present invention, the reflux pants for maintaining an infant having gastroesophageal reflux at a predetermined position on an inclined surface include means for stabilizing the upper torso of the infant. The means for stabilizing are adapted to be removably attached to the inclined bed for maintaining the infant in the predetermined position on the inclined bed. The reflux pants also include fastening means for removably attaching the means for stabilizing to the inclined bed and supporting means connected to the means for stabilizing for supporting the lower torso in the predetermined position.

The supporting means consists of pants adapted to fit on the lower torso of the infant. The pants include two leg holes into which the legs of the infant can be inserted, and means for opening the pants located substantially on at least one side of the pants.

The means for stabilizing consists of long straps each having one end releasably attached to the means for supporting. Another end of each strap is fixedly attached to the means for supporting.

The fastening means includes at least one short tab connected to the means for supporting, and at least one safety pin adapted to be pinned to the at least one tab. The tabs are shorter than the straps.

According to an embodiment of the present invention, the reflux pants for maintaining an infant having gastroesophageal reflux at a predetermined upright position on an inclined surface include a substantially rectangular panel adapted to be removably fastened around the lower torso of the infant in a closed position, strap means adapted to be releasably fastened around the upper torso of the infant, and fastening means for removably fastening the reflux pants to the inclined surface.

The substantially rectangular panel consists of a front portion adapted to be folded to cover the front of the lower torso of the infant, a rear portion adapted to be folded to cover the rear of the lower torso of the infant, and a middle portion between having a width smaller than the widths of the front portion and the rear portion. The front end rear portions each have an upper free end. When the substantially rectangular panel is in the closed position, openings are formed for receiving the legs of the infant.

The front portion includes first means for removably attaching the strap means to the upper free end of the front portion, and second means for removably attaching the upper free end of the rear portion to the upper free end of the front portion. The reflux pants also includes third means for removably attaching the strap means to the rear portion. The first, second, and third means for attaching comprises VELCRO strips.

The strap means consists of an H-shaped strap which includes two long sidearms. The long sidearms include first lower ends fixed to the front portion and second upper ends adapted to fold over the shoulders of the infant to be removably attached to the rear portion by the third means for removably attaching. The H-shaped strap also includes a transverse short arm connected between the two long sidearms at a given position along the sidearms.

The reflux pants also include two short tabs attached to the two long sidearms for removably attaching the reflux pants to the inclined surface by the fastening means. The fastening means consists of two safety pins adapted to pin the two short tabs to the inclined surface.

A pair of reflux pants are provided which are adapted to maintain an infant having gastroesophageal reflux at a predetermined position on an inclined surface; the pants comprise a front panel and a rear panel, the front and rear panels being integrally connected to each other by a fold line at respective lower surfaces thereof and having upper surfaces which are adapted to be selectively or detachably attached to each other by releasable connecting means. Two substantially parallel elongated straps extend upwardly from an upper edge of said front panel, said two elongated straps being connected by a third, relatively short strap attached to both of said parallel straps and being generally transversely arranged with respect to said straps and generally parallel with respect to said upper edge of said front panel. Each of said elongated straps has a first end attached to said front panel and a second, free end, which free ends are adapted to be detachably connected to a front surface of said rear panel when positioned about an infant. The reflux pants further comprise relatively short fourth and fifth straps extending from rear surfaces of said first and second straps, respectively, said fourth and fifth straps each having a first end attached to said first and second straps, respectively, and a second, free end, wherein the free ends of each of said fourth and fifth straps comprise means for attaching said pants to an inclined surface. The elongated straps are crisscrossed adjacent central portions thereof.

The first and second straps and the front and rear panels of the pants comprise means for stabilizing the upper torso of the infant when said infant is positioned at said predetermined position on said inclined surface. The pants further comprise first and second leg holes which separate side edges of said front and rear panels from each other, said leg holes comprising means for receiving respective legs of an infant. Each of said fourth and fifth straps includes at least one safety pin which is pinned to said free end and which is adapted to be attached to said inclined surface.

The free ends of said first and second straps are attached to said front surface of said rear panel, said front and rear panels are attached to each other at said lower edge and at respective upper portions thereof, and said first and second substantially parallel straps are crossed over each other at respective intermediate portions of said first and second elongated straps.

Further, a blank of material can be provided which is adapted to be folded into a pair of reflux pants for maintaining an infant having gastroesophageal reflux at a predetermined position on an inclined surface. The blank comprises a panel having first and second opposed end edges, said first and second end edges being substantially parallel to each other, and first and second side edges, each of said first and second side edges having first linear portions parallel to each other which are connected to opposite sides of said first end edge and second linear portions parallel to each other which are connected to opposite sides of said second side edge, said first and second linear portions along each of said first and second side edges being adjacent to curved portions of said arcuate cut outs which extend towards each other. The panel thus comprises first and second substantially wide panel portions along said first and second end edges and a third, relatively narrow portion integrally attached to said first and second panel portions and located between said first and second panel portions; said panel has an upper surface and a lower surface.

Attachment means for connecting the lower surface of said first panel portion to the upper surface of said second panel portion, and said attachment means are located on said first panel lower surface and said second panel upper surface, respectively.

Each of said elongated straps has a first end attached to an underside of said first panel portion lower surface and a second, free end spaced away from said first end edge of said panel, wherein each of the free ends of said first and second straps include, on respective upper surfaces thereof, means for attaching said first and second substantially parallel straps to the lower surface of said second panel portion, said second panel portion comprising means for attaching said second panel portion to said free ends of said first and second straps. A third strap connects said first and second straps to each other and is positioned in a substantially transverse fashion with respect to said first and second straps. A fourth strap is attached to a lower surface of said first strap, and a fifth strap is attached to a lower surface of said second strap, respectively.

Safety pins are attached to said free ends of said fourth and fifth straps, respectively. These safety pins comprise means for attaching said blank, when in a folded position, to an inclined surface. The blank is adapted to be folded into a pair of reflux pants, wherein when the blank is folded, said first and second end edges are attached to each other, respective leg holes for receiving respective legs of an infant are formed by said respective recesses, said first and second elongated straps are folded downwardly and crossed over each other, and the free ends of said first and second straps are attached to the front surface of said second panel portion.

BRIEF DESCRIPTION OF DRAWINGS

The invention will now be described with reference to the annexed drawings and description given by way of example, the same elements shown in the various figures being labelled with like reference numerals, in which.

DETAILED DESCRIPTION

Figure 1:
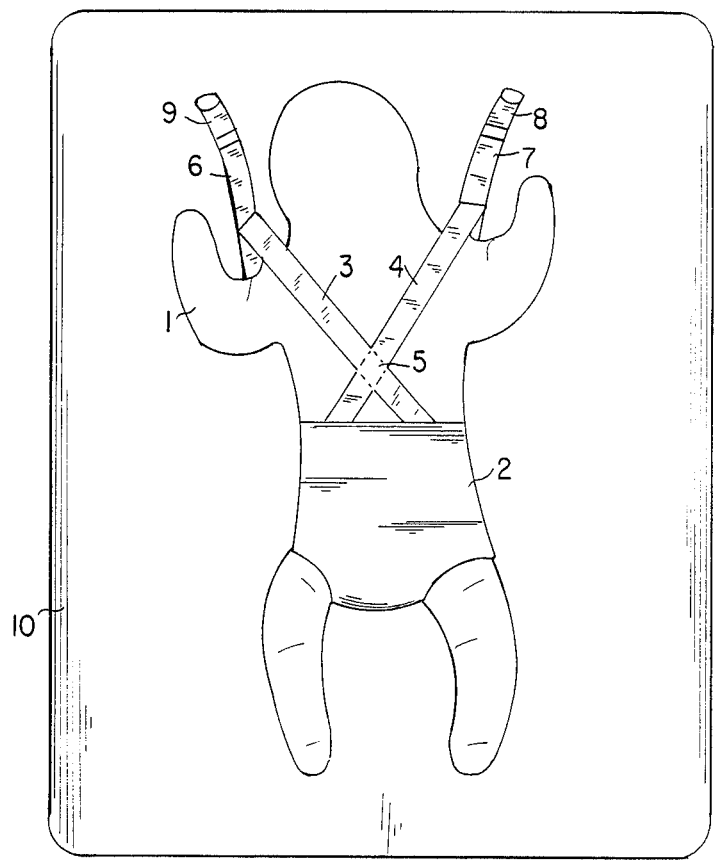
FIG. 1 is a view of an infant laying face down showing the rear portion of the reflux pants of the present invention.

FIG. 1 illustrates the reflux pants according to the present invention as they would appear on an infant laying face down on a surface. The reflux pants comprise a main torso portion 2 which covers the waist, hips, and crotch area, that is, the lower torso, of the baby 1. As shown from the rear, rear straps 3 and 4 cross each other at a point 5 substantially in the center of the infant's back. These criss-cross straps operate to stabilize the infant's chest in the proper position on the inclined surface. The pants further include upper tabs 6 and 7 which extend beyond the main body of the straps of the reflux pants. The free ends of tabs 6 and 7 are adapted to be attached to the inclined bed by, for example, safety pins 8 and 9, or by some other means for removably attaching tabs 6 and 7 to the bed.

Figure 2:
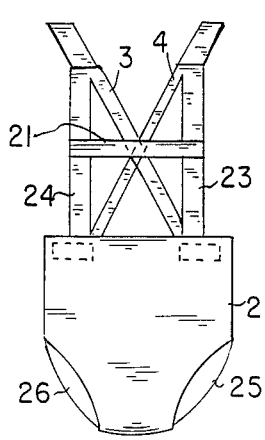
FIG. 2 shows the frontal view of the reflux pants in their closed position.

FIG. 2 illustrates a front view of the reflux pants according to the present invention. The reflux pants include an H-shaped strap with sidearms 23 and 24 and transverse arm 21. Tabs 6 and 7 are shorter than sidearms 23 and 24. The top portions of sidearms 23 and 24 of the H-shaped strap fold over towards the rear of the baby and form rear straps 3 and 4. The baby is inserted into the pants and his legs extend from leg holes 25 and 26.

Figure 3:
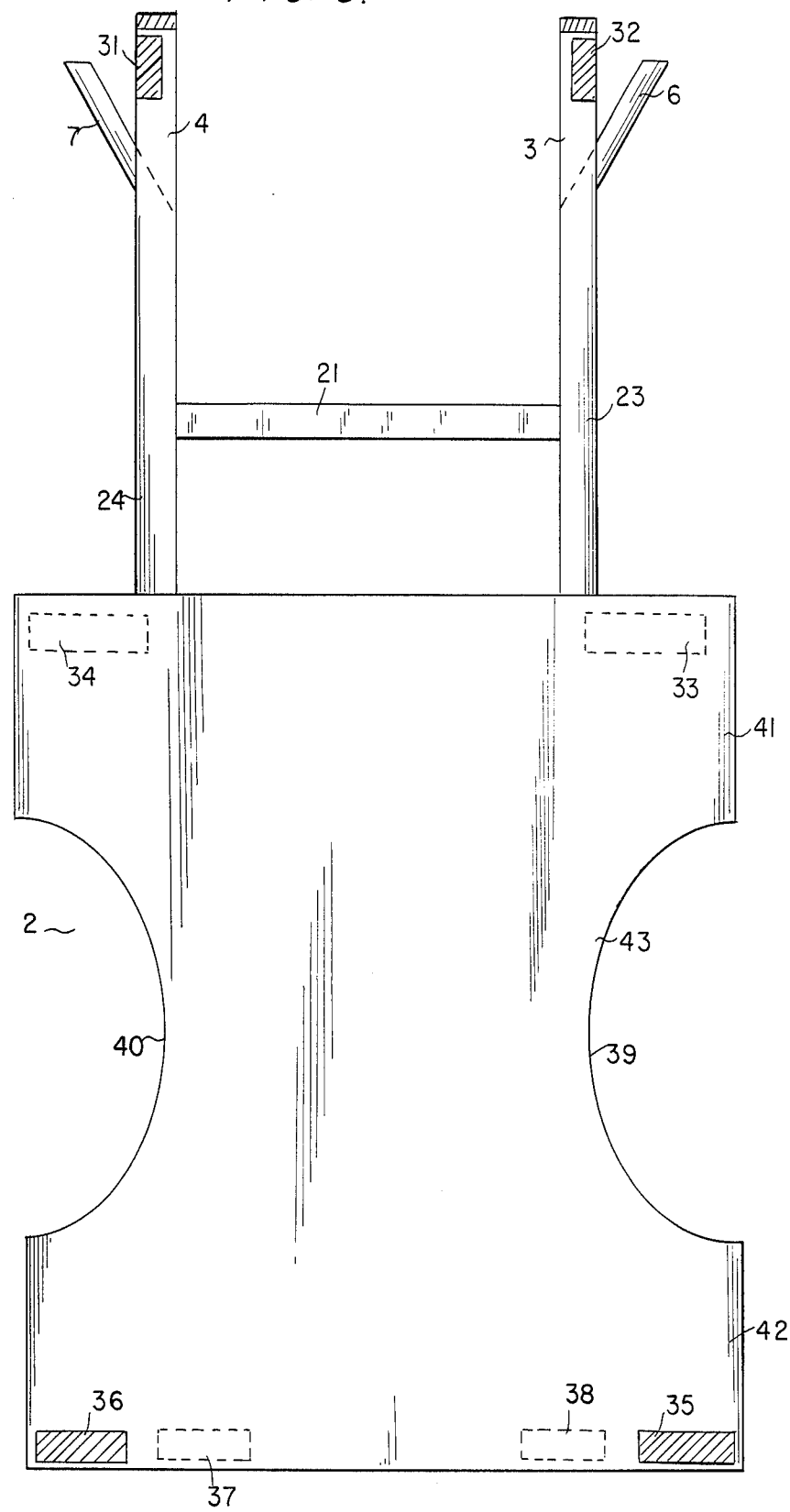
FIG. 3 shows a view of the reflux pants in the open extend position according to the present invention.

FIG. 3 illustrates the reflux pants of the present invention in their open position. Main body portion 2 comprises front portion 41 which covers the front of the baby when the pants are worn. Main body portion 2 also includes rear portion 42 which covers the rump of the baby when the baby is wearing the pants. The middle portion 43 consists of arcuate portions 39 and 40, which form the leg holes 25 and 26 when the reflux pants are folded into the diaper shaped pants. When rear portion 42 is folded over to meet front portion 41, VEL-CRO strips 35 and 36 meet and are attached to corresponding VELCRO portions 33 and 34. In this manner, the diaper is easily opened and closed. Wherever the word VELCRO is used hereinafter, it has a conventional meaning, i.e., there is one member having a plurality of loops and a second member having a plurality of hooks, which loops and hooks are adapted to releasably engage each other and facilitate engagement of two portions of the pants herein.

VELCRO portions 37 and 38, fitted to the outside of rear portion 42, are adapted to receive the VELCRO portions 31 and 32 attached to the top free ends of rear straps 3 and 4 of the H-shaped strap. When the pants are folded to form the diaper portion, rear straps 3 and 4 are folded over the shoulder of the baby and criss-crossed on the back of baby. The VELCRO strips 31 and 32 on rear straps 3 and 4 meet VELCRO portions 37 and 38 to secure the reflux pants on the baby.

Tabs 6 and 7 extend from the front portion of straps 23 and 24 and are adapted to be attached to the inclined surface by safety pins 8 and 9, as shown in FIG. 1.

Figure 4:
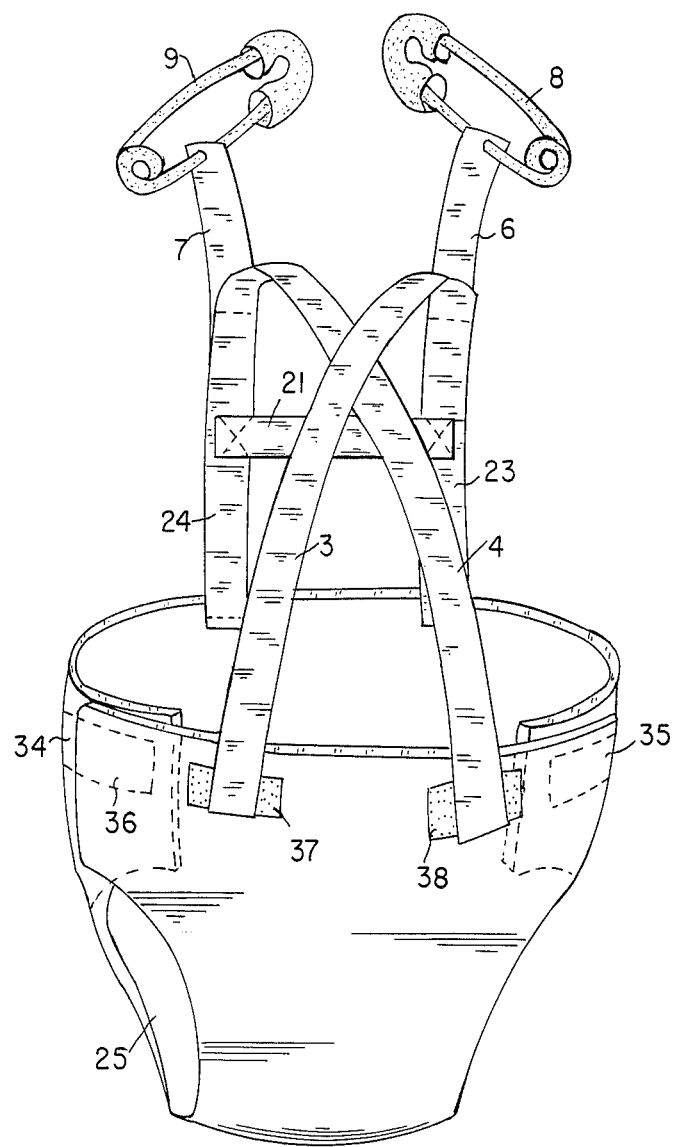
FIG. 4 shows a rear perspective view of the reflux pants in the folded position according to the present invention.

The reflux pants according to the present invention are made of material such as cotton or other washable material which can be sewn according to the pattern shown in the accompanying drawings. In order to place the baby in the resting position within the pants, the baby is laid face down on the open pants as shown in FIG. 3. The rear portion 42 is folded up between the legs of the baby as would be done for a normal pair of diapers. VELCRO strips 35 and 36 appearing on the inside of the rear portion 42, are attached to VELCRO strips 33 and 34 appearing on the outside of front portion 41. Rear straps 3 and 4 are folded back and are folded over the shoulders of the baby and criss-crossed in the center of the baby's back. Straps 3 and 4 are attached by fitting VELCRO strips 31 and 32 to VELCRO strips 37 and 38 appearing on the outside of rear portion 42. The pants are then pinned, using tabs 6 and 7 and safety pins 8 and 9, to the inclined bed 10. In this way, the infant's inclined position is assured, with both the chest and torso portions of the baby being stabilized. FIG. 4 illustrates, the reflux pants in the folded position, as shown from the rear.

Although the invention has been described with particular reference to a specific embodiment, it is understood that the invention contemplates any modifications within the skill of one of ordinary skill in the art and within the scope of the claims.

I claim:

1. A pair of reflux pants which are adapted to maintain an infant having gastroesophageal reflux at a predetermined position on an inclined surface, said pants comprising a front panel and a rear panel, the front and rear panels being integrally and foldably connected to each other at respective lower surfaces of said panels, each of said panels having first and second side portions, respectively, and an upper edge, said front panel side portions being adapted to be selectively attached to said rear panel side portions by releasable connecting means positioned on said panel side portions, wherein, when said panel side portions are attached to each other a continuous waistband is formed which is adapted to surround the waist of said infant, said reflux pants further comprising two substantially parallel, elongated straps extending upwardly from said upper edge of said front panel, said two elongated straps being connected to each other by a third, relatively short strap attached to both of said parallel straps, said third strap being generally transversely arranged with respect to said first and second straps and generally parallel with respect to said upper edge of said front panel, wherein each of said elongated straps has a first end which is attached to said front panel and a second, free end, the free end of each of said elongated straps being adapted to be detachably connected to said rear panel when said reflux pants are positioned about an infant, wherein said first, second, and third straps comprise means for detachably connecting said reflux pants about the torso of said infant and means for stabilizing said infant in a predetermined position on said inclined surface, said reflux pants further comprising relatively short fourth and fifth straps extending from said first and second straps, respectively, said fourth and fifth straps each having a first end attached to one of said first and second straps, respectively, and a second, free end, the free ends of each of said fourth and fifth straps comprising means for attaching said pants to said inclined surface.

2. A pair of reflux pants in accordance with claim 1, wherein said pants further comprise first and second leg holes which separate side edges of said front and rear panels from each other, each of said leg holes comprising means for receiving respective legs of an infant.

3. A pair of reflux pants in accordance with claim 1, wherein each of said fourth and fifth straps includes at least one safety pin pinned to a respective free end of said fourth and fifth straps, each of said fourth and fifth straps being adapted to be attached to said inclined surface.

4. A pair of reflux pants for maintaining an infant having gastroesophageal reflux at a predetermined position on an inclined surface, said parts comprising:

(a) a panel having first and second opposed end edges, said first and second end edges being substantially parallel to each other, and first and second side edges, each of said first and second side edges having first linear portions parallel to each other which are connected to opposite sides of said first end edge and second linear portions parallel to each other which are connected to opposite sides of said second end edge, the first and second linear portions along each of said first and second side edges being connected by a curved portion of an arcuate cut-out, said curved portions extending towards each other, wherein said panel comprises first and second substantially wide panel portions between said first and second edges and a third, relatively narrow portion integrally attached to said first and second panel portions and located between said first and second panel portions, each of said panel portions having an upper surface and a lower surface;

(b) means for connecting the lower surface of said first panel portion to the upper surface of said second panel portion, with complementary attachment means being located on said first panel portion lower surface and on said second panel portion upper surface, respectively, wherein said complementary attachment means are adapted to detachably connect the first linear portion of said first side edge to the first linear portion of the second side edge and the second linear portion of said first side edge to the second linear portion of said second side edge, wherein when the side edges are attached to each other they form a continuous waistband for surrounding an infant's waist;

(c) a pair of parallel straps, each of said parallel straps having a first end attached to a lower surface of said first panel portion and a second, free end spaced away from said first end edge, wherein each of the free ends of said first and second straps includes, on respective upper surfaces of said first and second straps, means for attaching said first and second substantially parallel straps to the lower surface of said second panel portion, said second panel portion comprising complementary attachment means for attaching said second panel portion to said free ends of said first and second straps;

(d) a third strap connecting said first and second straps to each other, said third strap being positioned in a substantially transverse position with respect to said first and second straps; and (e) a fourth strap attached to a lower surface of said first strap and a fifth strap attached to a lower surface of said second strap, respectively.

5. A pair of reflux pants in accordance with claim 4 further comprising safety pins attached to free ends of said fourth and fifth straps, respectively.

6. A pair of reflux pants in accordance with claim 5 wherein said safety pins comprise means for attaching said blank, when in a folded configuration, to an inclined surface.

7. A pair of reflux pants in accordance with claim 4 wherein said blank is adapted to be folded into a pair of reflux pants so that when said blank is folded, said first and second end edges are attached to each other, respective leg holes for receiving respective legs of an infant are formed by said respective recesses, said first and second elongated straps are folded downwardly and crossed over each other, and the free ends of said first and second straps are attached to the front surface of said second panel portion.

* * * * *

UNITED STATES PATENT AND TRADEMARK OFFICE
CERTIFICATE OF CORRECTION

PATENT NO. : 4,745,926

DATED : May 24, 1988

INVENTOR(S) : Dana L. HLUSKO

It is certified that error appears in the above-identified patent and that said Letters Patent is hereby corrected as shown below:

At column 2, line 19, insert ---is--- after "invention" and before "to".

At column 2, line 67, insert ---,--- after "straps" and before "each".

At column 6, line 16, change "VELCR0" to ---VELCRO--- (final letter O, not zero).

At column 6, line 42, delete "," after "illustrates" and before "the".

Signed and Sealed this

Twenty-fifth Day of April, 1989

Attest:

DONALD J. QUIGG

Attesting Officer

Commissioner of Patents and Trademarks